United States Patent [19]
Cathala et al.

[11] Patent Number: 6,140,526
[45] Date of Patent: Oct. 31, 2000

[54] METHOD FOR OBTAINING ORGANOSILANES IMPLEMENTING A REDISTRIBUTION REACTION

[75] Inventors: Max Cathala; Pascale Colin, both of Chassieu; Michel Dardare, Chaponnay; Françoise Igersheim, Lyons, all of France

[73] Assignee: Rhodia Chimie, Courbevoie, France

[21] Appl. No.: 09/202,100

[22] PCT Filed: Jun. 11, 1997

[86] PCT No.: PCT/FR97/01034

§ 371 Date: Sep. 7, 1999

§ 102(e) Date: Sep. 7, 1999

[87] PCT Pub. No.: WO97/47629

PCT Pub. Date: Dec. 18, 1997

[30] Foreign Application Priority Data

Jun. 12, 1996 [FR] France ................................ 96 07569

[51] Int. Cl.[7] .................................................. C07F 7/08
[52] U.S. Cl. .................................................. 556/469
[58] Field of Search .......................................... 556/469

[56] References Cited

U.S. PATENT DOCUMENTS

| | | | |
|---|---|---|---|
| 3,980,686 | 9/1976 | Lefort et al. | 556/469 |
| 4,567,286 | 1/1986 | Lepage et al. | 556/469 |
| 5,654,459 | 8/1997 | Kropfgans et al. | 556/469 |
| 5,866,707 | 2/1999 | Herzig | 556/469 |

FOREIGN PATENT DOCUMENTS

| | | | |
|---|---|---|---|
| 2119477 | 8/1972 | France | 556/469 |

*Primary Examiner*—Paul F. Shaver
*Attorney, Agent, or Firm*—Jean-Louis Seugnet

[57] ABSTRACT

Improved method for obtaining organosilanes comprising: a redistribution reaction between a chlorinated organohydrogenosilane and an organo-substituted and optionally chlorinated silane, the distribution reaction taking place in the presence of a sufficient amount of a catalyst consisting of a Lewis acid of formula (3) $M(X)_d$ in which: M represents a metal selected among Ti, Fe, Cu, Ag, Zn, Cd, Hg, Al, Ga, In, B, Sn, Pb, Sb, and Bi; X represents a halogen atom; d represents the valency of metal M; and separation by distillation of the chlorinated organohydrogenosilane produced by redistribution; the said method being characterized in that, after redistribution, a redistribution catalyst inhibiting compound is used. This catalyst is selected among the fluid polyorganosiloxanes (POS) having a viscosity at 25° C. not exceeding 5000 mPa·s and is used in such proportions that the ratio r=number of gram-atoms of metal M given by the catalyst/number of gram-atoms of oxygen given by the inhibitor does not exceed 0.9.

13 Claims, No Drawings

METHOD FOR OBTAINING ORGANOSILANES IMPLEMENTING A REDISTRIBUTION REACTION

The subject-matter of the present invention is an improved method for obtaining organosilanes and the invention relates particularly to an improved method for obtaining organosilanes in which a so-called redistribution reaction is involved. More particularly, the present invention relates to an improved method for obtaining organosilanes in which is involved a redistribution reaction between a chlorinated organohydrosilane and an organosubstituted and optionally chlorinated silane, in order to result in a product comprising a redistributed chlorinated organohydrosilane, which is extracted from the reaction mixture by distillation.

Without this being limiting, the present invention is very especially targeted at a redistribution reaction between an alkylhydrodichlorosilane and a trialkylchlorosilane, in order to result in a product comprising a redistributed dialkylhydrochlorosilane. This redistributed dialkylhydrochlorosilane is a synthetic agent which is particularly valued in a great many varied applications, for example, preparation of organosilicon monomers or more condensed base compounds.

Dialkylhydrochlorosilane is one of the by-products from the synthesis of alkylchlorosilanes according to a conventional and well known procedure which consists in reacting alkyl chloride with silicon, in the presence of a copper catalyst, in order to form alkylchlorosilanes. In this synthesis, the dialkyldichlorosilane is the main product. Compounds of the trialkylchlorosilane, alkyltrichlorosilane and alkylhydrodichlorosilane type are also obtained, in addition to the abovetargeted dialkylhydrochlorosilane by-product.

Due to the industrial interest of these by-products in the chemistry of silicones and in particular of the dialkylhydrochlorosilane, such as dimethylhydrochlorosilane, numerous proposals for procedures for obtaining these by-products have seen the light of day. One of the few which has proved itself in this respect is that which consists in carrying out a redistribution reaction between, for example, an alkylhydrodichlorosilane and a trialkylchlorosilane or between an alkylhydrodichlorosilane and a tetraalkylsilane. This redistribution results in the targeted dialkylhydrochlorosilanes, which are extracted from the reaction mixture by distillation.

In this context, numerous redistribution reactions of organosilanes, cutting and redistributing silicon-alkyl, silicon-chlorine or silicon-hydrogen bonds, in the presence of various catalysts, such as Lewis acids, are known. French Patent FR-A-2,119,477 clearly illustrates this technique for the preparation of dialkylhydrochlorosilane by redistribution/distillation. In accordance with the teaching of this patent, methylhydrodichlorosilane and trimethylchlorosilane are reacted in a methylhydrodichlorosilane/trimethylchlorosilane molar ratio of the order of 0.5 in the presence of a catalyst formed by $AlCl_3$. The reaction mixture is placed in a reactor, under an autogenous pressure of the order of 3 to $5 \times 10^5$ Pa, and maintained for several hours at a temperature of the order of 85 to 170° C. The Applicant Company has repeated this procedure of the prior art and it has observed that the yield of the distillation, which is carried out at the end of the process in order to separate the redistributed dimethylhydrochlorosilane from the reaction mixture, is abnormally low and peaks at approximately 71%. It must be considered that such results are unsatisfactory with regard to industrial profitability.

In this state of knowledge, one of the essential objects of the present invention consists of the development of an improved method for obtaining organosilanes in which is involved a redistribution reaction between a chlorinated organohydrosilane and an organosubstituted and optionally chlorinated silane, in order to result in a product comprising a redistributed chlorinated organohydrosilane, which is extracted from the reaction mixture by distillation, which method ought to be characterized by distillation yields of final targeted product, the redistributed chlorinated organohydrosilane, which are markedly superior to those of the known redistribution/distillation methods.

Another essential object of the invention is to provide a method of the type of that targeted above and which is particularly simple to carry out and is economical.

In order to be able to achieve all these objects, and others too, the Applicant Company has had the credit of demonstrating a side reaction phenomenon induced by the catalyst during the distillation. This is because it could be demonstrated that conventional redistribution catalysts, such as, for example, $AlCl_3$, catalyse a dismutation reaction of the chlorinated organohydrosilane produced by redistribution. Such a dismutation results in the conversion of the said redistribution product into by-products of the optionally chlorinated organohydrosilane type, on the one hand, and chlorinated organosilane type, on the other hand. That is how, for example, $Me_2HSiCl$ is converted to $Me_2SiH_2$ and to $Me_2SiCl_2$, due to this dismutation side reaction (the abbreviation Me denotes the monovalent $CH_3$ radical).

It is clear that such a phenomenon can only be entirely harmful to the yield of redistributed chlorinated organohydrosilane, such as, for example, $Me_2HSiCl$.

The credit of the Applicant Company has not been limited to this discovery of the technical problem existing in known redistribution/distillation reactions. This is because, entirely surprisingly and unexpectedly, it has also found a means of reducing, indeed eliminating, the dismutation side reaction by inhibiting the redistribution catalyst, once it has fulfilled its role in the first stage of the method.

It follows that the present invention relates to an improved method for obtaining organosilanes comprising:

a redistribution reaction between a chlorinated organohydrosilane of formula (1)

$$(R)_a(H)_bSiCl_{4-a-b}$$

and an organosubstituted and optionally chlorinated silane of formula (2)

$$(R')_cSiCl_{4-c},$$

in which formulae: a=1 or 2; b=1 or 2; a+b=3; c=1, 2, 3 or 4; and the symbols R and R' are alike or different and each represent a linear or branched $C_1$-$C_6$ alkyl radical or a $C_6$-$C_{12}$ aryl radical; the said redistribution reaction taking place in the presence of an effective amount of a catalyst consisting of a Lewis acid of formula (3) $M(X)_d$, in which: M represents a metal selected from Ti, Fe, Cu, Ag, Zn, Cd, Hg, Al, Ga, In, B, Sn, Pb, Sb and Bi; X represents a halogen atom; and d represents the valency of the metal M;

and a separation by distillation of the chlorinated organohydrosilane produced by redistribution; the said method being characterized in that, after the redistribution, at least one compound which inhibits the redistribution catalyst is introduced, this compound corresponding to the following definitions:

it is chosen from fluid polyorganosiloxanes (abbreviated to POS) having a viscosity at 25° C. at most equal to 5000 mPa•s;

it is used in proportions such that the ratio:

$$r = \frac{\text{number of moles of } M \text{ metal atoms contributed by the catalyst}}{\text{number of moles of oxygen atoms contributed by the inhibitor}}$$

is equal to or less than 0.9.

In accordance with the present invention, advantage is taken of the inhibition of the redistribution catalyst, once the latter has fulfilled its function. This neutralization of the catalytic activity makes it possible to reduce as much as possible, indeed eliminate, the dismutation side reactions which conventionally took place during the distillation. Thus, the targeted redistributed chlorinated organohydrosilanes are produced, at the end of distillation, with better yields than previously.

Another highly advantageous effect is observable when the inhibitor compound is used, which constitutes a preferred embodiment of the present invention, in proportions such that the ratio r mentioned above is situated very specifically within the range from 0.6 to 0.9.

This other highly advantageous effect consists of the elimination of the appearance and of the deposition of solid materials in the distillation residues, which then have a homogeneous look. In the case of the absence of inhibitor compound or in the case of the use of insufficient proportions of inhibitor compound (corresponding to values of r of greater than 0.9) or in the case of the use of excessively high proportions of inhibitor compound (corresponding to values of r of less than 0.6), the result is distillation residues which then have a two-phase look, due to the appearance and the deposition of solid materials. The Applicant Company believes that these solid materials may be: catalyst particles, in the case of the use of insufficient proportions of inhibitor compound; amorphous crystals of a complex formed from the catalyst and the inhibitor silicone compound, in the case of the use of excessively high proportions of inhibitor compound.

The inhibitor silicone compound can be:
(i) a linear or substantially linear POS composed of units of formula (4), terminated at one of the ends of the chains by a unit of formula (5) and at the other end by a unit of formula (6),
(2i) a cyclic POS composed of units of formula (4),
(3i) a mixture of several species (i) or (2i) with one another,
(4i) a mixture of one or more species (i) with one or more species (2i),

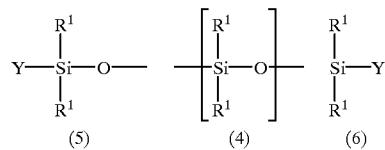

in which formulae:
the $R^1$ symbols are alike or different and each represent a linear or branched $C_1$-$C_8$ alkyl radical optionally substituted by one or more halogen(s), such as, for example, methyl, ethyl, propyl, octyl or 3,3,3-trifluoropropyl; a $C_5$-$C_8$ cycloalkyl radical, such as, for example, cyclohexyl or cycloheptyl; or a $C_6$-$C_{12}$ aryl radical or an aralkyl radical having a $C_6$-$C_{12}$ aryl part and a $C_1$-$C_4$ alkyl part, optionally substituted on the aromatic part by one or more halogen(s), $C_1$-$C_3$ alkyl(s) and/or $C_1$-$C_3$ alkoxy, such as, for example, phenyl, xylyl, tolyl, benzyl, phenylethyl, chlorophenyl or dichlorophenyl;

the Y symbols are alike or different and each represent: either an $R^1$ radical or an $OR^2$ radical, where $R^2$ is a hydrogen atom or a linear or branched $C_1$-$C_3$ alkyl radical.

Linear POS (i) is understood to mean POS which do not have more than 3% of units other than the units of formulae (4), (5) and (6), for example units of formulae $R^1SiO_{3/2}$ (T) and/or $SiO_2$ (Q), the % shown expressing the number of T and/or Q units per 100 silicon atoms.

The inhibitor silicone compound preferably consists of a fluid of type (i), (2i), (3i) or (4i) having a viscosity at 25° C. which is at most equal to 1000 mPa•s and at least 60% by number of the $R^1$ symbols of which represent methyl radicals.

Examples of inhibitor silicone compounds which are highly suitable are:
as linear POS (i): polydimethylsiloxanes which are blocked at each of the chain ends by a trimethylsiloxy unit [in the formulae (4), (5) and (6): $R^1$=Y=$CH_3$] or by a hydroxyl group [in the formulae (4), (5) and (6): $R^1$=$CH_3$ and Y=OH] and which have a viscosity at 25° C which is between 5 and 300 mPa•s;
as cyclic POS (2i): cyclic polydimethylsiloxanes exhibiting from 3 to 9 units of formula (4), where $R^1$=$CH_3$;
and their various possible mixtures of (3i) or (4i) type.

The Lewis acids which are employed as catalysts in the present method are preferably chlorides and bromides.

Examples of catalysts which are highly suitable are: $TiCl_4$, $FeCl_3$, CuCl, AgCl, $ZnCl_2$, $AlCl_3$, $SnCl_2$, $BiCl_3$ and their various mixtures. The catalyst which is very especially well suited is $AlCl_3$.

The catalysts are used in proportions by weight generally ranging from 0.1 to 10% and preferably from 0.5 to 5% with respect to the total weight of the silanes of formulae (1) and (2) charged at the start. Proportions by weight which are very especially preferred are those ranging from 1 to 4% with respect to the same reference.

Another important parameter of the method according to the invention relates to the moment at which the inhibitor silicone compound is introduced. In any case, it is preferable for the latter to be introduced when the redistribution reaction is complete.

Furthermore, it being known that the redistribution reaction is generally carried out at temperatures of between 50° C. and 200° C. (advantageously under autogenous pressure) and that the reaction mixture is subsequently cooled before distillation, it is possible to anticipate introducing the inhibitor compound:
either at the redistribution temperature, before cooling,
or after returning the reaction mixture to this cooling temperature,
or before and after the said cooling.

In this context, the two preferred embodiments of the method according to the invention are given below:
According to a first embodiment:
the redistribution reaction is carried out at a temperature of between 50 and 200° C., preferably between 80 and 150° C., advantageously under autogenous pressure,
the reaction mixture is subsequently cooled to a temperature of less than 40° C., preferably of less than 30° C. and more preferably still of between 10 and 30° C., the inhibitor silicone compound is then introduced, and, finally, the targeted chlorinated organohydrosilane, produced by redistribution, is separated by distillation.

According to a second embodiment:

the redistribution is carried out at a temperature of between 50 and 200° C., preferably between 80 and 150° C., advantageously under autogenous pressure, the inhibitor silicone compound is introduced, so that the redistribution is interrupted, the reaction mixture is subsequently cooled to a temperature of less than 40° C., preferably of less than 30° C. and more preferably still of between 10 and 30° C., and, finally, the targeted chlorinated organohydrosilane is separated by distillation.

As regards the parameters of the method (duration, temperature, pressure), it will be specified, to clarify our views, that it is highly advantageous for the redistribution temperature to be, for example, of the order of 90 to 120° C., while the ideal pressure is based around from 3 to $5 \times 10^5$ Pa. The duration of the redistribution reaction depends on the stoichiometry of the reaction, as well as on the temperature. By way of example, it is possible to indicate that it will be of the order of 1 to 3 hours.

It is very especially preferable for the cooling of the reaction mixture after redistribution to correspond to a temperature of the order of 15° C.

Before introducing the inhibitor, the reaction mixture is returned to atmospheric pressure, if needs be, for example by degassing.

The inhibitor silicone compound is advantageously introduced slowly, for example over one or several tens of minutes, for example 20 to 30 minutes. The incorporation of the inhibitor compound generally results in a slight rise in temperature, as well as a significant evolution of gas and possibly the formation of a white precipitate.

The stage which follows is thus the distillation, preferably at atmospheric pressure, which results in a distillate comprising the desired redistribution chlorinated organohydrosilane and a two-phase or homogenous distillation residue, depending on the amount of inhibitor silicone compound employed.

As regards the two types of silanes allowed to react, that is to say the chlorinated organohydrosilane of formula (1) and the organosubstituted and optionally chlorinated silane of formula (2), it will be noted that the R and R' symbols can be chosen, for example, from methyl, ethyl, propyl, isopropyl, butyl, hexyl, phenyl, naphthyl and diphenyl radicals.

The R and R' symbols are preferably alike or different and each represent a linear or branched $C_1$-$C_3$ alkyl radical or a phenyl radical.

In any case, the R and R' symbols which are very especially preferred are alike or different and each represent a methyl or a phenyl.

The method according to the present invention applies well to the implementation of a redistribution reaction between the chlorinated organohydrosilane (1) of formula $RHSiCl_2$ and the organosubstituted and chlorinated silane (2) of formula $R'_3SiCl$ (in this case, a=1, b=1 and c=3), in which formulae the R and R' symbols have the general meanings given above, in the presentation of the invention, with respect to the formulae (1) and (2).

The method according to the present invention applies very particularly well to the implementation of a redistribution reaction between the chlorinated organohydrosilane (1) of formula $RHSiCl_2$ and the organosubstituted and chlorinated silane (2) of formula $R'_3SiCl$ (in this case, a=1, b=1 and c=3), in which formulae the R and R' symbols are alike or different and each represent a linear or branched $C_1$-$C_3$ alkyl radical or a phenyl radical.

The method according to the present invention applies very especially well to the implementation of a redistribution reaction between the chlorinated organohydrosilane (1) of formula $RHSiCl_2$ and the organosubstituted and chlorinated silane (2) of formula $R'_3SiCl$, in which formulae the R and R' symbols are alike or different and each represent a methyl or phenyl radical.

Generally, in carrying out the method according to the present invention, the reactant of chlorinated organohydrosilane type of formula (1) can be present in the medium of the redistribution reaction in a proportion of at least 10 mol % with respect to the mixture: chlorinated organohydrosilane of formula (1) + organosubstituted and optionally chlorinated silane of formula (2).

Preferably, the molar ratio:

$$\frac{\text{chlorinated organohydrosilane of formula (1)}}{\text{organosubstituted silane of formula (2)}}$$

is between 0.1 and 2. More preferably still, this molar ratio is between 0.3 and 0.7.

In the context of the redistribution reaction, to the implementation of which the method according to the invention applies very especially well, for example involving $MeHSiCl_2$ and $Me_3SiCl$ as starting silanes (1) and (2), at the end a chlorinated organohydrosilane produced by redistribution, consisting of $Me_2HSiCl$, and the compound $Me_2SiCl_2$ are recovered. It should be noted that this silane $Me_2SiCl_2$ is essentially a product of the redistribution reaction but it can also originate, when it takes place, from the dismutation side reaction which has been spoken of above, where a portion of the redistributed silane $Me_2HSiCl$ is converted to $Me_2SiH_2$ and $Me_2SiCl_2$.

The method according to the invention makes it possible to significantly increase the yields of redistributed chlorinated organohydrosilane (for example $Me_2HSiCl$), while simplifying the synthetic operating procedures (redistribution/distillation).

The devices used for the implementation of the method are conventional chemical engineering devices entirely within the scope of a person skilled in the art.

The examples which follow will make it possible to better understand all the alternative forms and the advantages (processability) of the method according to the invention by underlining, by comparative tests, the increases in yield obtained.

EXAMPLES

A) Inhibitor silicone compounds employed:

POS 1: α,ω-dihydroxylated linear polydimethylsiloxane oil with a viscosity at 25° C. equal to 50 mPa•s, of formula:

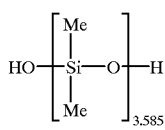

and having the following characteristics: calculated molecular mass=283.3 g; number of oxygen atoms per one mole of oil=4.59;

POS 2: cyclic polydimethylsiloxane oil comprising 4 dimethylsiloxy units with a viscosity at 25° C. equal to 2 mPa•s and having the following characteristics: calculated molecular mass=296 g; number of oxygen atoms per one mole of oil=4;

POS 3: cyclic polydimethylsiloxane oil comprising 5 dimethylsiloxy units with a viscosity at 25° C. equal to 2.5 mPa•s and having the following characteristics: calculated molecular mass=370 g; number of oxygen atoms per one mole of oil=5.

B) Procedure:

(I) Tests without locking up of catalyst:

Comparative Example 1

913 g of $Me_3SiCl$ and 483 g of $MeHSiCl_2$, in order to obtain an $MeH/Me_3$ molar ratio equal to 0.5, are charged with stirring to a 2 liter stainless steel reactor purged beforehand with nitrogen. The catalyst, i.e. 42 g of anhydrous aluminium chloride, is added to this mixture. The reactor is closed and the pressure is adjusted to $10 \times 10^5$ Pa with nitrogen and to the value of atmospheric pressure. Stirring is provided by a Rushton turbine. The stirring speed is set at 1000 revolutions/min. Heating is carried out to 100° C. and the pressure settles down at $4.5 \times 10^5$ Pa. The temperature is maintained at 100° C. for 2 hours. The reactor is cooled to 20° C. and the residual pressure of 1.5 to $2 \times 10^5$ Pa is removed by degassing. 1387 g of the reaction mixture, comprising 193 g of $Me_2HSiCl$ and 3% by weight of aluminium chloride, are separated by distillation at atmospheric pressure. A distillate comprising the dimethylhydrochlorosilane and a heterogeneous distillation residue with suspended $AlCl_3$ are obtained.

The distillates and residues are analysed by vapour phase chromatography. $Me_2HSiCl$ in distillate: 136 g.

II) Tests with locking up of catalyst:

Example 1

915 g of $Me_3SiCl$ and 483 g of $MeHSiCl_2$, in order to obtain an $MeH/Me_3$ molar ratio equal to 0.5, are charged with stirring to a 2 liter stainless steel reactor purged beforehand with nitrogen.

The catalyst, i.e. 42 g of anhydrous aluminium chloride, is added to this mixture. The reactor is closed and the pressure is adjusted to $10 \times 10^5$ Pa with nitrogen and then to atmospheric pressure. Stirring is provided by a Rushton turbine. The stirring speed is set at 1000 revolutions/min. Heating is carried out to 100° C. and the pressure settles down at $4.5 \times 10^5$ Pa. The temperature is maintained at 100° C. for 2 hours. The reactor is cooled to 15° C. The residual pressure of $1.5 \times 10^5$ Pa is removed by degassing. 149 g of inhibitor compound POS 1 are introduced into the reactor over 20 minutes. The temperature rises to 18.5° C. A significant evolution of gas and the formation of a white precipitate are observed. 1557 g of reaction mixture, comprising 185.7 g of $Me_2HSiCl$ and the inactive catalyst, are separated by distillation at atmospheric pressure. A distillate comprising the dimethylhydrochlorosilane and a two-phase distillation residue are obtained.

The distillates and residues are analysed by vapour phase chromatography. $Me_2HSiCl$ in distillate: 185 g.

Example 2

915 g of $Me_3SiCl$ and 483 g of $MeHSiCl_2$, in order to obtain an $MeH/Me_3$ molar ratio equal to 0.5, are charged with stirring to a 2 liter stainless steel reactor purged beforehand with nitrogen.

The catalyst, i.e. 42 g of anhydrous aluminium chloride, is added to this mixture. The reactor is closed and the pressure is adjusted to $10 \times 10^5$ Pa with nitrogen and then to atmospheric pressure. Stirring is provided by a Rushton turbine. The stirring speed is set at 1000 revolutions/min. Heating is carried out to 100° C. and the pressure settles down at $4.5 \times 10^5$ Pa. The temperature is maintained at 100° C. for 2 hours. The reactor is cooled to 15° C. The residual pressure of $1.5 \times 10^5$ Pa is removed by degassing. 66 g of inhibitor compound POS 1 are introduced into the reactor over 20 minutes. The temperature rises to 18.5° C. A significant evolution of gas and the formation of a white precipitate are observed. 1476 g of reaction mixture, comprising 199.6 g of $Me_2HSiCl$ and the inactive catalyst, are separated by distillation at atmospheric pressure. A distillate comprising the dimethylhydrochlorosilane and a two-phase distillation residue are obtained.

The distillates and residues are analysed by vapour phase chromatography. $Me_2HSiCl$ in distillate: 199 g.

Example 3

915 g of $Me_3SiCl$ and 483 g of $MeHSiCl_2$, in order to obtain an $MeH/Me_3$ molar ratio equal to 0.5, are charged with stirring to a 2 liter stainless steel reactor purged beforehand with nitrogen.

The catalyst, i.e. 42 g of anhydrous aluminium chloride, is added to this mixture. The reactor is closed and the pressure is adjusted to $10 \times 10^5$ Pa with nitrogen and then to atmospheric pressure. Stirring is provided by a Rushton turbine. The stirring speed is set at 1000 revolutions/min. Heating is carried out to 100° C. and the pressure settles down at $4.5 \times 10^5$ Pa. The temperature is maintained at 100° C. for 2 hours. 58.5 g of inhibitor compound POS 3 are introduced into the reactor over 10 minutes. No increase in the pressure is recorded. The reactor is subsequently cooled to 20° C. The residual pressure of 1.5 to $2 \times 10^5$ Pa is removed by degassing. 1462 g of reaction mixture, comprising 196.8 g of $Me_2HSiCl$ and the inactive catalyst, are separated by distillation at atmospheric pressure. A distillate comprising the dimethylhydrochlorosilane and a two-phase distillation residue are obtained.

The distillates and residues are analysed by vapour phase chromatography. $Me_2HSiCl$ in distillate: 196.4 g.

Example 4

915 g of $Me_3SiCl$ and 483 g of $MeHSiCl_2$, in order to obtain an $MeH/Me_3$ molar ratio equal to 0.5, are charged with stirring to a 2 liter stainless steel reactor purged beforehand with nitrogen.

The catalyst, i.e. 42 g of anhydrous aluminium chloride, is added to this mixture. The reactor is closed and the pressure is adjusted to $10 \times 10^5$ Pa with nitrogen and then to atmospheric pressure. Stirring is provided by a Rushton turbine. The stirring speed is set at 1000 revolutions/min. Heating is carried out to 100° C. and the pressure settles down at $4.5 \times 10^5$ Pa. The temperature is maintained at 100° C. for 2 hours. The reactor is cooled to 20° C. The residual pressure of 1.5 to $2 \times 10^5$ Pa is removed by degassing. 46.2 g of inhibitor compound POS 2 are introduced into the reactor over 10 minutes. A slight exotherm without evolution of gas is observed. 1416 g of reaction mixture, comprising 206 g of $Me_2HSiCl$ and the inactive catalyst, are separated by distillation at atmospheric pressure. A distillate comprising the dimethylhydrochlorosilane and a two-phase distillation residue are obtained.

9

The distillates and residues are analysed by vapour phase chromatography. Me$_2$HSiCl in distillate: 200 g.

Example 5

915 g of Me$_3$SiCl and 483 g of MeHSiCl$_2$, in order to obtain an MeH/Me$_3$ molar ratio equal to 0.5, are charged with stirring to a 2 liter stainless steel reactor purged beforehand with nitrogen.

The catalyst, i.e. 42 g of anhydrous aluminium chloride, is added to this mixture. The reactor is closed and the pressure is adjusted to 10×10$^5$ Pa with nitrogen and then to atmospheric pressure. Stirring is provided by a Rushton turbine. The stirring speed is set at 1000 revolutions/min. Heating is carried out to 100° C. and the pressure settles down at 5×10$^5$ Pa. The temperature is maintained at 100° C. for 2 hours. 45 g of inhibitor compound POS 3 are introduced into the reactor over 10 minutes. The reactor is subsequently cooled to 20° C. The residual pressure of 1.5 to 2×10$^5$ Pa is removed by degassing. 1424 g of reaction mixture, comprising 194.3 g of Me$_2$HSiCl and the inactive catalyst, are separated by distillation at atmospheric pressure. A distillate comprising the dimethylhydrochlorosilane and a two-phase distillation residue are obtained.

The distillates and residues are analysed by vapour phase chromatography. Me$_2$HSiCl in distillate: 190.4 g.

Example 6

915 g of Me$_3$SiCl and 491 g of MeHSiCl$_2$, in order to obtain an MeH/Me$_3$ molar ratio equal to 0.5, are charged with stirring to a 2 liter stainless steel reactor purged beforehand with nitrogen.

The catalyst, i.e. 42 g of anhydrous aluminium chloride, is added to this mixture. The reactor is closed and the pressure is adjusted to 10×10$^5$ Pa with nitrogen and then to atmospheric pressure. Stirring is provided by a Rushton turbine. The stirring speed is set at 1000 revolutions/min. Heating is carried out to 100° C. and the pressure settles down at 5×10$^5$ Pa. The temperature is maintained at 100° C. for 2 hours. 36 g of inhibitor compound POS 3 are introduced into the reactor over 10 minutes. The reactor is subsequently cooled to 20° C. The residual pressure of 1.5 to 2×10$^5$ Pa is removed by degassing. 543.8 g of reaction mixture, comprising 71 g of Me$_2$HSiCl and the inactive catalyst, are separated by distillation at atmospheric pressure. A distillate comprising the dimethylhydrochlorosilane and a homogeneous distillation residue are obtained.

The distillates and residues are analysed by vapour phase chromatography. Me$_2$HSiCl in distillate: 69.3 g.

Comparative Example 2

909 g of Me$_3$SiCl and 476 g of MeHSiCl$_2$, in order to obtain an MeH/Me$_3$ molar ratio equal to 0.5, are charged with stirring to a 2 liter stainless steel reactor purged beforehand with nitrogen.

The catalyst, i.e. 42 g of anhydrous aluminium chloride, is added to this mixture. The reactor is closed and the pressure is adjusted to 10×10$^5$ Pa with nitrogen and then to atmospheric pressure. Stirring is provided by a Rushton turbine. The stirring speed is set at 1000 revolutions/min. Heating is carried out to 100° C. and the pressure settles down at 5×10$^5$ Pa. The temperature is maintained at 100° C. for 2 hours. 23.7 g of inhibitor compound POS 3 are introduced into the reactor over 10 minutes. The reactor is subsequently cooled to 20° C. The residual pressure of 1.5 to 2×10$^5$ Pa is removed by degassing. 518 g of reaction mixture, comprising 73.5 g of Me$_2$HSiCl and the inactive catalyst, are separated by distillation at atmospheric pressure. A distillate comprising the dimethylhydrochlorosilane and a two-phase distillation residue are obtained.

The distillates and residues are analysed by vapour phase chromatography. Me$_2$HSiCl in distillate: 41.2 g.

The results obtained are summarized in the following Table I. RY represents the yield of the distillation.

TABLE 1

| Examples | CATALYST AlCl$_3$ Weight (g) | Moles of Al atoms | INHIBITOR Inhibitor nature | Weight (g) | Moles of oxygen atoms | Molar ratio r | Me$_2$HSiCl (RY %) | LOOK OF THE RESIDUE H = homogeneous T = two-phase |
|---|---|---|---|---|---|---|---|---|
| Comparative Ex. 1 | 42 | 0.315 | none | | | | 70.4 | T |
| Example 1 | 42 | 0.315 | POS 1 | 149 | 2.414 | 0.13 | 99.6 | T |
| Example 2 | 42 | 0.315 | POS 1 | 66 | 1.069 | 0.29 | 99.7 | T |
| Example 3 | 42 | 0.315 | POS 3 | 58.5 | 0.791 | 0.39 | 99.8 | T |
| Example 4 | 42 | 0.315 | POS 2 | 46.2 | 0.624 | 0.50 | 97.1 | T |
| Example 5 | 42 | 0.315 | POS 3 | 45 | 0.608 | 0.52 | 97.9 | T |
| Example 6 | 42 | 0.315 | POS 3 | 36 | 0.486 | 0.65 | 97.6 | H |
| Comparative Ex. 2 | 42 | 0.315 | POS 3 | 23.7 | 0.320 | 0.98 | 56.1 | T |

What is claimed is:

1. A process for the preparation of organosilanes comprising the steps of:

1) carrying out a redistribution reaction between a chlorinated organohydrosilane of formula (1): (R)$_a$(H)$_b$SiCl$_{4-a-b}$ and an organosubstituted and optionally chlorinated silane of formula (2): (R')$_c$SiCl$_{4-c}$, wherein: a=1 or 2; b=1 or 2; a+b=3; c=1, 2, 3 or 4; and the symbols R and R' are alike or different and each represent a linear or branched C$_1$-C$_6$ alkyl radical or a C$_6$-C$_{12}$ aryl radical; said redistribution reaction taking place in the presence of an effective amount of a catalyst consisting of a Lewis acid of formula (3) M(X)$_d$, wherein: M represents a metal selected from the group consisting of Ti, Fe, Cu, Ag, Zn, Cd, Hg, Al, Ga, In, B, Sn, Pb, Sb and Bi; X represents a halogen atom; and d represents the valency of the metal M;

2) then, adding at least one inhibitor of the redistribution catalyst, said inhibitor being a fluid polyorganosiloxane having a viscosity at 25° C. at most equal to 5000 mPa•s and being used in proportions such that the ratio:

$$r = \frac{\text{number of moles of } M \text{ metal atoms contributed by the catalyst}}{\text{number of moles of oxygen atoms contributed by the inhibitor}}$$

is equal to or less than 0.9; and 3) carrying out a separation by distillation of the chlorinated organohydrosilane produced by redistribution.

2. A process according to claim 1, wherein r is from 0.6 to 0.9.

3. A process according to claim 1, wherein the inhibitor is
(i) a linear or substantially linear polyorganosiloxane comprising units of formula (4), terminated at one of the ends of the chains by a unit of formula (5) and at the other end by a unit of formula (6),
(2i) a cyclic polyorganosiloxane comprising units of formula (4),
(3i) a mixture of species (i) and species (2i), or
(4i) a mixture of one or more species (i) with one or more species (2i),

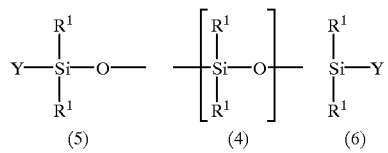

wherein:
  the $R^1$ symbols are alike or different and each represent a linear or branched $C_1$-$C_8$ alkyl radical optionally substituted by one or more halogens; a $C_5$-$C_8$ cycloalkyl radical; or a $C_6$-$C_{12}$ aryl radical or an aralkyl radical having a $C_6$-$C_{12}$ aryl part and a $C_1$-$C_4$ alkyl part, optionally substituted on the aromatic part by one or more halogens, $C_1$-$C_3$ alkyl radicals or $C_1$-$C_3$ alkoxy radicals; and
  the Y symbols are alike or different and each represent: either an $R^1$ radical or an $OR^2$ radical, where $R^2$ is a hydrogen atom or a linear or branched $C_1$-$C_3$ alkyl radical.

4. A process according to claim 3, wherein the inhibitor is a fluid of species (i), (2i), (3i) or (4i) having a viscosity at 25° C. of at most equal to 1000 mPa•s and at least 60% by number of the $R^1$ symbols represent methyl radicals.

5. A process according to claim 1, wherein the Lewis acid catalyst is a chloride or a bromide.

6. A process according to claim 5, wherein the catalyst is $TiCl_4$, $FeCl_3$, CuCl, AgCl, $ZnCl_2$, $AlCl_3$, $SnCl_2$, $BiCl_3$ or their various mixtures.

7. A process according to claim 1, wherein the quantity of catalyst is from 0.1 to 10% by weight with respect to the total weight of the silanes of formulae (1) and (2) charged in step 1).

8. A process according to claim 1, wherein in step 1) the redistribution reaction is carried out at a temperature of between 50 and 200° C., then the temperature is lowered at less than 40° C., and then, in step 2), the inhibitor is added, and, finally, in step 3) the chlorinated organohydrosilane, produced by redistribution, is separated by distillation.

9. A process according to claim 1, wherein the redistribution reaction is carried out under autogenous pressure.

10. A process according to claim 1, wherein: in step 1) the redistribution reaction is carried out at a temperature of between 50 and 200° C., then, in step 2) the inhibitor is added, so that the redistribution reaction is interrupted, the temperature is lowered to a temperature of less than 40° C., and, finally, in step 3), the targeted chlorinated organohydrosilane is separated by distillation.

11. A process according to claim 9, wherein the redistribution reaction is carried out under autogenous pressure.

12. A process according to any one of claim 9 the chlorinated organohydrosilane of formula (1) and the organosubstituted and optionally chlorinated silane of formula (2), and wherein the R and R' symbols are alike or different and each represent a linear or branched $C_1$-$C_3$ alkyl radical or a phenyl radical.

13. A process according to claim 1, wherein the redistribution reaction is carried out between the chlorinated organohydrosilane (1) of formula $RHSiCl_2$ and the organosubstituted and chlorinated silane (2) of formula $R'_3SiCl$ wherein a=1, b=1, and c=3.

* * * * *